(12) United States Patent
Hayami

(10) Patent No.: US 9,364,082 B2
(45) Date of Patent: Jun. 14, 2016

(54) CONSTANT-TEMPERATURE DEVICE PROVIDED WITH ROTATING SPECIMEN TABLE

(75) Inventor: Makoto Hayami, Fukuyama (JP)

(73) Assignee: Rorze Corporation, Hiroshima (JP)

( * ) Notice: Subject to any disclaimer, the term of this patent is extended or adjusted under 35 U.S.C. 154(b) by 306 days.

(21) Appl. No.: 14/126,392

(22) PCT Filed: Jun. 11, 2012

(86) PCT No.: PCT/JP2012/064875
§ 371 (c)(1),
(2), (4) Date: Dec. 13, 2013

(87) PCT Pub. No.: WO2012/173074
PCT Pub. Date: Dec. 20, 2012

(65) Prior Publication Data
US 2014/0117824 A1    May 1, 2014

(30) Foreign Application Priority Data

Jun. 14, 2011 (JP) ................................ 2011-131824

(51) Int. Cl.
*A47B 49/00* (2006.01)
*B01L 7/00* (2006.01)
(Continued)

(52) U.S. Cl.
CPC ............... *A47B 49/004* (2013.01); *A47B 81/00* (2013.01); *B01J 3/03* (2013.01); *B01J 3/04* (2013.01);
(Continued)

(58) Field of Classification Search
CPC .... A47B 49/004; A47B 81/00; F25D 25/027; B01J 3/04; F04D 13/024; F04D 13/025; F04D 13/026; F04D 13/027; F04D 29/048; A61M 1/1015; F04C 15/0069
USPC ....................... 417/420; 435/286.7; 312/249.2
See application file for complete search history.

(56) References Cited

U.S. PATENT DOCUMENTS 1,687,149 A * 10/1928 Shauer .................. F25D 25/027
                                                                108/104
1,732,113 A * 10/1929 Van Der Meer ........ B60S 13/02
                                                                108/139
(Continued)

FOREIGN PATENT DOCUMENTS

WO    WO2010/001873    1/2010
WO    WO2010/001874    1/2010

OTHER PUBLICATIONS

International Preliminary Report on Patentability.

*Primary Examiner* — Daniel J Troy
*Assistant Examiner* — Timothy M Ayres
(74) *Attorney, Agent, or Firm* — Merek Blackmon & Voorhees LLC

(57) ABSTRACT

Provided is a constant-temperature device which comprises conveyance mechanism and which can operate stably over a long period of time even when installed in an atmosphere of a sterilization gas having strong oxidative properties, such as hydrogen peroxide gas, or a high temperature environment during dry-heat sterilization operations. A drive unit for a rotatably operated specimen table (10) on which a specimen is placed, in an incubation chamber, is arranged outside of the incubation chamber, and the drive-force from the drive unit is transmitted by means of magnetic coupling. Furthermore, ring-shaped seal packing (22), in which a lip (24) is formed, is arranged above and below a base plate (13) provided to the specimen plate (10), and a seal plate (23) is arranged along the entire perimeter of the base plate (13) at the portion which makes contact with the lip (24), thus a bearing (17) and/or a drive portion are isolated from high-temperature atmospheres and in-chamber atmospheres having strong oxidative properties, preventing damage due to high temperatures or sterilization gas.

8 Claims, 7 Drawing Sheets

(51) Int. Cl.
    *A47B 81/00*    (2006.01)
    *B01J 3/03*     (2006.01)
    *B01J 3/04*     (2006.01)
    *C12M 1/00*     (2006.01)
    *H02K 49/10*    (2006.01)
    *G01N 35/00*    (2006.01)

(52) U.S. Cl.
    CPC ....... *B01L 7/00* (2013.01); *C12M 47/16* (2013.01); *H02K 49/108* (2013.01); *B01L 2200/0689* (2013.01); *B01L 2200/141* (2013.01); *B01L 2300/0803* (2013.01); *B01L 2300/1838* (2013.01); *G01N 2035/00356* (2013.01)

(56) References Cited

U.S. PATENT DOCUMENTS

| | | | | |
|---|---|---|---|---|
| 1,941,906 A * | 1/1934 | Marinsky | ............... | F25D 25/027 108/103 |
| 2,279,558 A * | 4/1942 | Clerc | ............... | A47F 3/0404 312/305 |
| 2,556,854 A * | 6/1951 | Spears | ............... | B01F 13/0827 310/104 |
| 2,638,558 A * | 5/1953 | Rankin | ............... | H02K 49/108 310/104 |
| 2,768,316 A * | 10/1956 | Neiss | ............... | H02K 49/108 123/41.11 |
| 2,951,447 A * | 9/1960 | Casassa | ............... | F02M 37/08 310/104 |
| 2,968,248 A * | 1/1961 | Carter | ............... | F02M 37/08 417/420 |
| 3,299,819 A * | 1/1967 | McCoy | ............... | H02K 49/108 310/104 |
| 3,572,981 A * | 3/1971 | Pearson | ............... | F04B 1/0426 417/415 |
| 4,266,914 A * | 5/1981 | Dickinson | ............... | F04D 13/024 417/360 |
| 4,304,532 A * | 12/1981 | McCoy | ............... | F16J 15/50 310/104 |
| 4,312,752 A * | 1/1982 | Malik | ............... | A01K 63/047 210/167.22 |
| 4,635,894 A * | 1/1987 | Sammons | ............... | A47B 49/00 108/103 |
| 5,470,744 A * | 11/1995 | Astle | ............... | C12M 41/14 160/241 |
| 5,775,665 A * | 7/1998 | Haskin | ............... | A47B 11/00 248/349.1 |
| 6,475,776 B1 * | 11/2002 | Higuchi | ............... | C12M 23/48 422/561 |
| 7,314,341 B2 * | 1/2008 | Malin | ............... | B65G 1/045 414/331.02 |
| 7,785,867 B2 * | 8/2010 | Tamaoki | ............... | C12M 23/48 435/286.2 |
| 8,282,268 B2 * | 10/2012 | Karkos, Jr. | ............... | A47J 43/0465 366/273 |
| 8,925,346 B2 * | 1/2015 | Natarajan | ............... | 312/408 |
| 2006/0105450 A1 * | 5/2006 | Owen | ............... | G01N 35/0099 435/303.3 |
| 2006/0270027 A1 * | 11/2006 | Shaw | ............... | B01L 1/02 435/303.3 |

* cited by examiner

CONSTANT-TEMPERATURE DEVICE PROVIDED WITH ROTATING SPECIMEN TABLE

FIELD OF THE INVENTION

The present invention relates to a constant-temperature device that at least keeps temperature stable and automatically carries in and out a container storing a specimen to be a test object.

BACKGROUND OF THE INVENTION

The constant-temperature device is widely used as a device to store specimens used for culturing and testing microbes or cells. The constant-temperature device has various instruments to keep environmental condition such as temperature, humidity and carbon dioxide concentration in a thermostatic chamber storing a large number of specimens to be cultured and tested. In case of culture, the thermostatic chamber is kept in a high humidity state equal to or more than 90% of humidity at temperature 37° C. In addition, culturing and testing continue for a long time, and therefore, in the process, it is necessary to change culture medium mixed with waste matter to new one if necessary by periodically examining and analyzing condition of each specimen.

Accordingly, many automatic constant-temperature devices with a memorization means, an operating means and a transport means have been devised up to date. These devices are provided with functions to automatically carry out taking in and out the container storing the specimen, to delivery to examining step and analyzing step, and to control the specimen condition, thereby enabling to efficiently carrying out culture and test for a long period.

When atmospheric unwanted bacteria, previous cultured cells or microbes remain in the thermostatic chamber, the constant-temperature device adversely affects the objective cells and microorganisms in new culturing and testing. Therefore, an operation called sterilization is required for the inside of the thermostatic chamber to remove bacteria before starting culturing or testing. The conventional constant-temperature device with an automatic conveyance mechanism has adopted a sterilization method for irradiating ultraviolet rays or a sterilization method for wiping off with medicinal solution. However, there recently appear constant-temperature devices with an automatic conveyance mechanism that have no motors and no electronic members in the thermostatic chamber, thereby enabling use of a sterilization method called dry sterilization for killing the unwanted bacteria by keeping inside temperature equal to or more than 130° C.

PRIOR ART

Patent Literature

Patent literature 1: WO2010/001873

DISCLOSURE OF THE INVENTION

Problems to be Solved by the Invention

A constant-temperature device 1 with an automatic conveyance mechanism disclosed in Patent literature 1 adopts a method in which a specimen table on which a plurality of specimen shelves each saving a container storing a specimen for culturing or testing are detachably arranged in a thermostatic chamber, and a plurality of driven magnets placed on the specimen table are magnetically coupled with a plurality of driving magnets located on positions corresponding to the driven magnets outside the thermostatic chamber, and a rotating magnetic field is generated by drive-force given from a drive source to the driving magnets and transferred to the driven magnets to be magnetically coupled. Ball casters and wheels are installed on an under surface of the specimen table at fixed intervals, the specimen table can rotate and move to a predetermined position as being supported to the ball casters and the wheels. In addition, a conveyor robot with a lifting means for carrying in and out the container storing the specimen is provided to the outside of the thermostatic chamber. The specimen table is rotated and moved at the position where the conveyor robot can access, so that the conveyor robot can access to the desired shelf of the desired specimen shelf.

According to the above-mentioned structure, no members easily affected by high temperature and high humidity such as motors or electrical members are arranged inside the thermostatic chamber, and therefore, it is possible to carry out dry heat sterilization for keeping the inside of the thermostatic chamber in high temperature. Further, it is possible to operate stably without any hitch even if a culture environment for keeping the inside of the thermostatic chamber in the humidity of 90% or more.

However, recently, instead of the dry-heat-sterilization, a lot of sterilization methods for sterilizing by filling hydrogen peroxide vapor due to heating and vaporizing inside the thermostatic chamber, which is called hydrogen peroxide sterilization, begin to be adopted. According to these methods, the hydrogen peroxide vapor is filled in the incubation chamber, and the bacteria is killed by sterilizing power of hydrogen peroxide. In the dry heat sterilization, it takes several hours up to cultivable temperature after beginning to heat the inside of the thermostatic chamber. However, the hydrogen peroxide sterilization can be completed in a short time of approximately one hour, thereby shortening downtimes from the culture end to the next culture start drastically.

However, in the conventional constant-temperature device with the automatic conveyance mechanism, it is difficult to perform the above-mentioned hydrogen peroxide sterilization. The reason is that the hydrogen peroxide has high corrosive nature to corrode structures made from iron or aluminum inside the chamber. Specially, in case of movable members, even if surface treatment is performed to prevent corrosion, the treated surface is scraped due to a long-period operation, thereby corroding the exposed metal surface. In addition, lubricant is used for metal components such as the ball casters for supporting the specimen table on a plurality of positions as a rolling element located inside the thermostatic chamber and the bearings for rotatably supporting the resin-made wheel having heat resistant characteristics, to prevent friction and wearing. A minute amount of moisture included in the lubricant and moisture permeating from the high humidity environment into the lubricant become a hotbed of bacteria. Hydrogen peroxide gas cannot sufficiently sterilize the bacteria in the moisture inside the lubricant. If the bacteria remains in a culture chamber after sterilizing, the bacteria contaminates the specimen in next culturing. Accordingly, good culture results are not obtained. Places to be corroded and places where remaining of bacteria is predicted come to exist in each of the bearings because the rolling elements for supporting the specimen table are dispersed at a plurality of places.

Accordingly, it is really necessary to provide a constant-temperature device with an automatic conveyance mechanism that is resistant to the corrosion action of hydrogen peroxide and that is constructed so that the lubricant of the hotbed of bacteria should not be exposed to the atmosphere inside chamber.

Means to Solve the Problem

This invention was created to solve the above mentioned problems effectively, wherein a bearing having a center of rotating shaft at a position meeting a rotation center of rotating field in a vertical axis direction is provided in a closed space of the constant-temperature device in which highly corrosive chemicals are used so as to be gathered in one place and freely attached and detached from the constant-temperature device.

To settle the above-mentioned problems, the constant-temperature device of the invention includes a thermostatic chamber having a closed space and walls for surrounding the closed space, a rotating magnetic field generation means that gives rotating field having a rotation center in a vertical axis direction from an underside of a floor face of a bottom portion of the walls to the closed space through the floor face, and a base plate detachably located in the closed space of the thermostatic chamber. The base plate is provided with a bearing having a center of a rotating shaft at a position meeting the rotation center in the vertical axis direction. To an upper side rotating shaft over the bearing, is connected a specimen plate mounted specimen shelves each saving a container storing a specimen, and to a lower side rotating shaft under the bearing, is connected a magnet plate having a plurality of driven magnets. The driven magnets are magnetically coupled with the rotating field transmitted through the walls of the thermostatic chamber to rotate the rotating shaft in accordance with the rotating field.

According to the above-mentioned structure, in the thermostatic chamber, it is possible to rotate the specimen plate rotatably supported to the base plate through the bearing by rotating the magnetically coupled driven magnets following the rotating field located under the floor of the thermostatic chamber. It is possible to arrange a device for generating rotating field outside the thermostatic chamber, and therefore, even if the inside of the thermostatic chamber is filled with hydrogen peroxide atmosphere, the device is never corroded by the oxidative effect. Here, an axial loads resistance bearing made of metal like stainless, ceramic or resin can be used as the bearing of this invention. It is preferable that the bearing made of resin such as PTFE (polytetrafluoroethylene), PEEK (polyetheretherketone), PPS (polyphenylene sulfide), which do not need the lubricant, or the ceramic bearing made of zirconia, silicon carbide and silicon nitride should be used.

Further preferably, to isolate the bearing from an outside air, ring-shaped seal packings each having a lip are provided between the base plate and the specimen plate and/or the rotating shaft, and between the base plate and a plate fixed the driven magnets or the rotating shaft.

According to the above-mentioned structure, the specimen plate, the magnet plate, the base plate, the rotating shaft, and the ring-shaped seal packings mounted on the specimen plate and the magnet plate come into contact with the bearing over the entire periphery, and therefore, an environment in which the bearing is placed can be interrupted from the high humidity atmosphere inside the thermostatic chamber and the hydrogen peroxide gas atmosphere. Therefore, it is possible to use a bearing made of materials which need the lubricant.

Further a gas may be introduced into a space surrounded on the ring-shaped seal packing and the specimen plate and/or the rotating shaft and the bearing, and besides, a space surrounded on the base plate and the plate fixed the driven magnets and/or the rotating shaft.

According to the above-mentioned structure, it is possible to keep positive pressure by introducing a gas such as clean air in the space surrounded by the base plate and the rotating shaft and the ring-shaped seal packing, thereby preventing leakage of corrosive gases such as water vapor and hydrogen peroxide. Therefore, the axial loads resistance bearing can prevent from being corroded, thereby enabling rotations of the specimen table over a long time in the thermostatic chamber. In introducing the gas into the space, holes communicating with the space are pierced in the base plate, and tubes connected to the holes are formed. In addition, it is preferable that another hole should be pierced in the base plate as an exhaust port to exhaust the gas outside the thermostatic chamber through the tubes. As a gas, can be used clean air, dry air, carbon dioxide gas and nitrogen that are filtrated by a filter having a thickness equal to or less than 0.1 μm.

Further it is desirable that materials of the ring-shaped seal packings should be selected from oxidation resistant flexible high polymer such as fluororubber, vinyl acetate ethylene resin, hydrogenated nitrile rubber, ethylene propylene rubber, acrylic rubber. Above all, in case of the ring-shaped seal packing made of fluororubber, it is preferable that the dry heat sterilization, which keeps the inside of the thermostatic chamber in an environment equal to or more than 130° C., can be performed in addition to the sterilization by the sterilization gas such as hydrogen peroxide gas. In addition, it is desirable that the base plate should have a seal plate whose surface is smoothed at a position where the lip of the ring-shaped seal packing comes into contact with.

Further, in case the seal plate is provided, it is possible to make a portion with which the lip comes into contact and a portion with which the lip does not come into contact into separate parts. Accordingly, it is possible to reduce manufacturing cost of the base plate. Besides, it is preferable to select material of the seal plate from fluorine resin such as polytetrafluoroethylene or silicone resin having heat resisting properties and a little frictional resistance. In addition, in case of the seal plate made of metal, it is preferable to perform surface coat processing by fluorine with a little frictional resistance.

Further, the specimen plate may have a resin-made pad at the portion coming into contact with the floor face of the thermostatic chamber. In addition, fixing the specimen plate with screws through the resin-made pad can prevent the floor face of the thermostatic chamber from being damaged. Further, the specimen table can be easily detached from the floor face of the thermostatic chamber by detaching the screws. Accordingly, it is possible to easily perform wiping operation after sterilization.

Besides, the resin-made pad can be made of polyethersulfone, polyether ether ketone resin, silicone resin or polytetrafluoroethylene, but it is preferable to use fluorine resin or silicone resin such as polytetrafluoroethylene with heat resisting properties and a little frictional resistance.

Effects of Invention

According to the present invention, it is possible to remove the base plate from the thermostatic chamber together with the bearing by detachably arranging the base plate having the bearing in the closed space surrounded by the walls of the thermostatic chamber. The floor face forming a magnetic gap of magnetic coupling has no structures for transmitting rotations to its surface, and therefore, when removing the base plate, a wiping operation after sterilization can be easily performed. On the other hand, the bearing is positioned at the rotation center of the rotating magnetic field to intensively support the load of the specimen table, thereby smoothly rotating the specimen plate on which the specimen shelves are put. In addition, it is possible to facilitate sealing from the chemical agents because the bearing is concentrated in one place and not dispersed.

It is desirable to use the ring-shaped seal packing as a structure for sealing. Providing with the ring-shaped seal packing enhances the durability, and besides, introducing cleaned air into the axial loads resistance bearing portion remarkably enhances the durability. Accordingly, even after performing the sterilization by sterilization gas with strong oxidizing properties represented by hydrogen peroxide, the specimen table can stably work. In addition, it is possible to shorten stop time of culture in comparison with the dry heat sterilization and the other sterilization because hydrogen peroxide can be utilized for sterilizing. Therefore, even if the present invention is adopted to an automated incubator, it is possible to enhance production efficiency.

PREFERRED EMBODIMENT OF THE INVENTION

Figure 1:
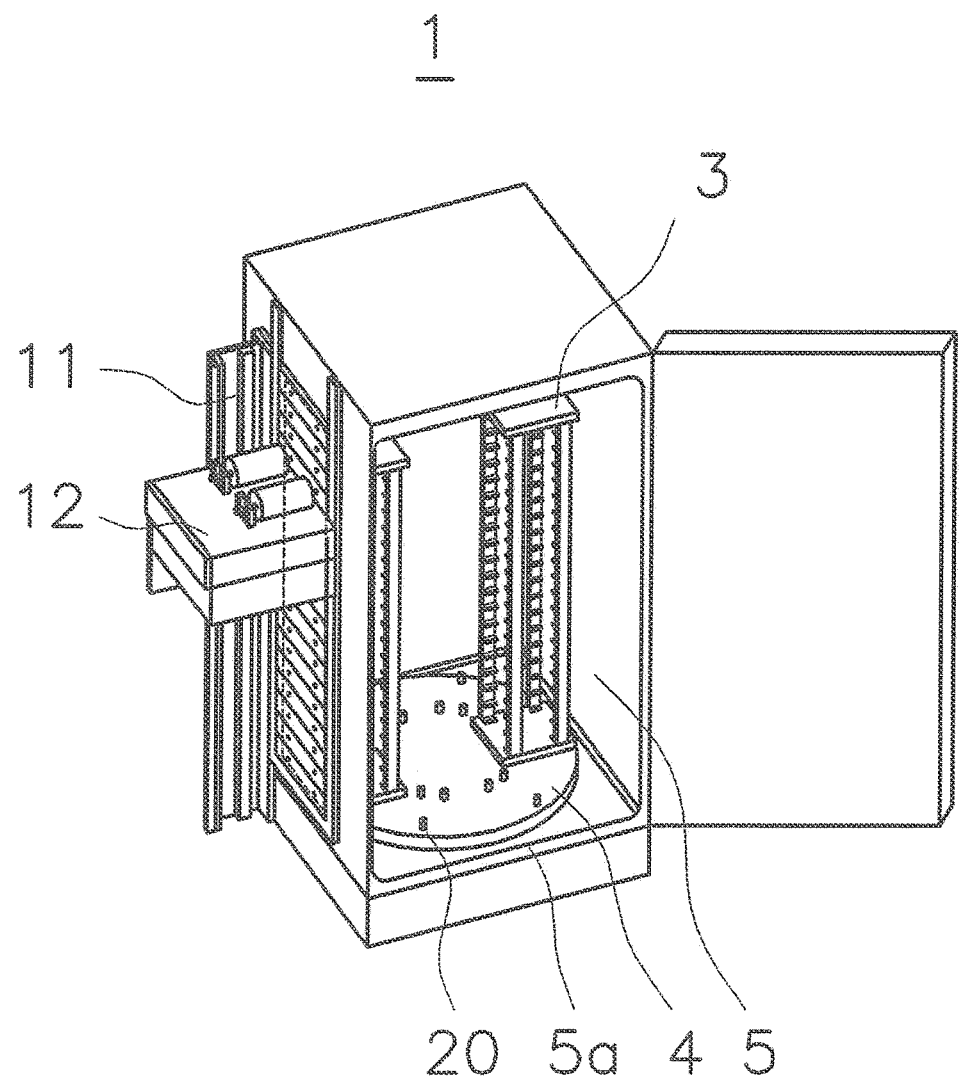
FIG. 1 is a perspective view showing a conventional constant-temperature device with an automatic conveyance mechanism.
Figure 2:
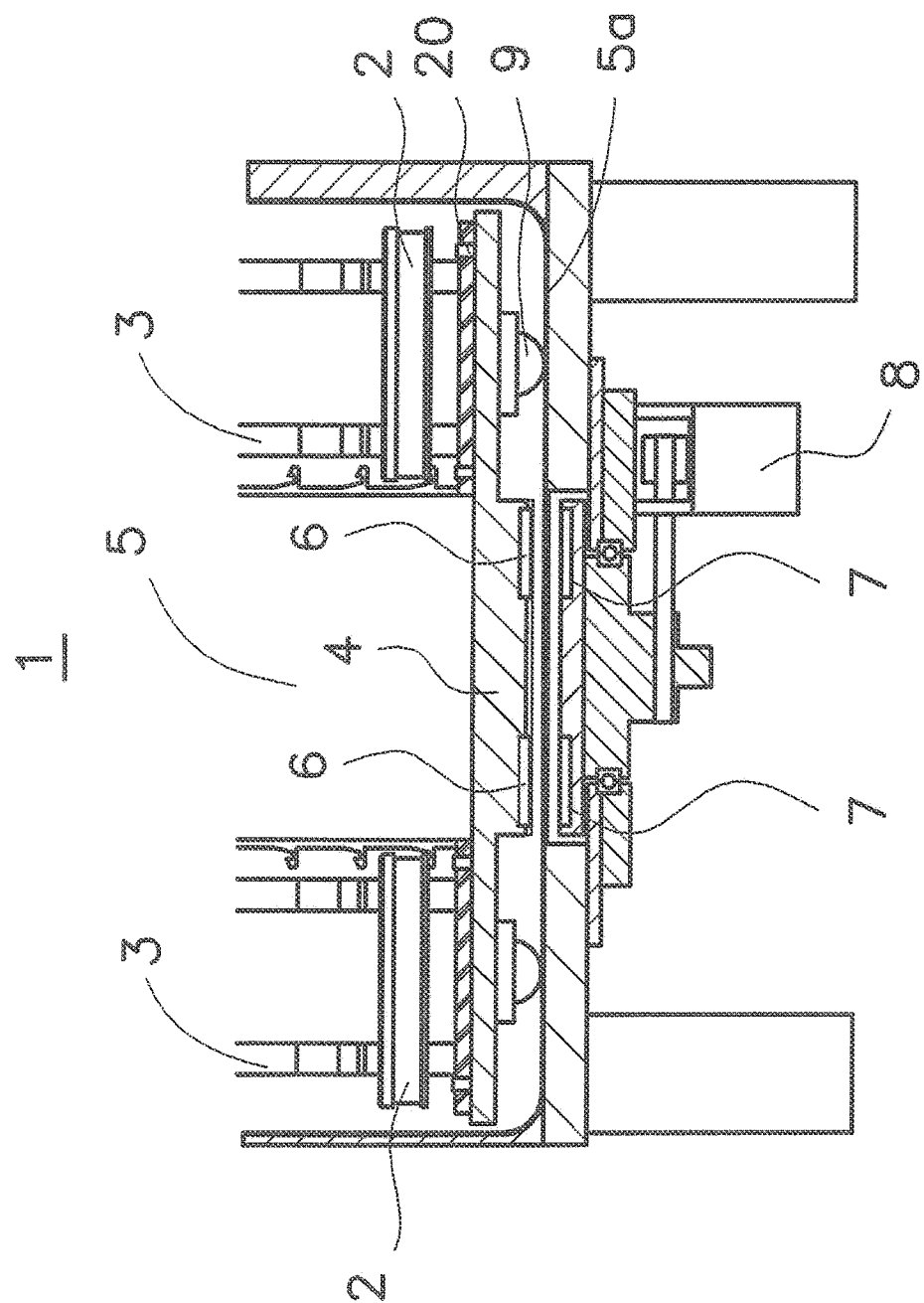
FIG. 2 is a cross-sectional view showing around a specimen table of the conventional constant-temperature device with the automatic conveyance mechanism.
Figure 3:
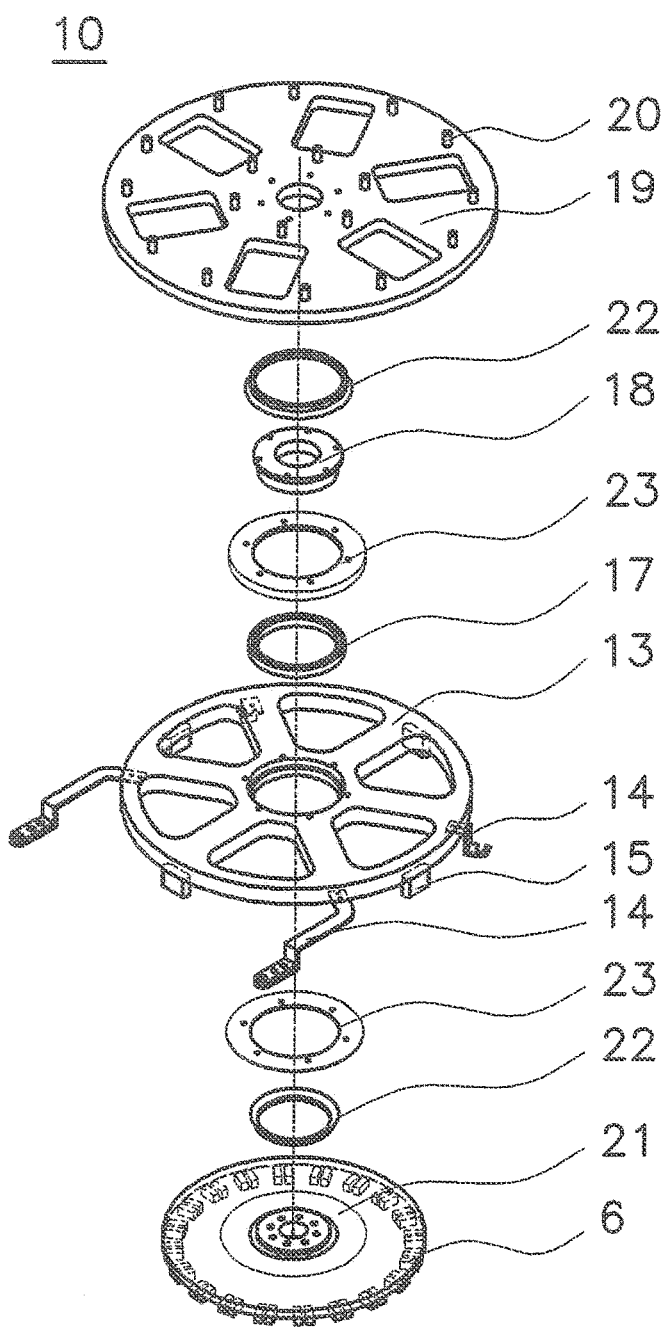
FIG. 3 is an exploded view of a specimen table of a first example.
Figure 4:
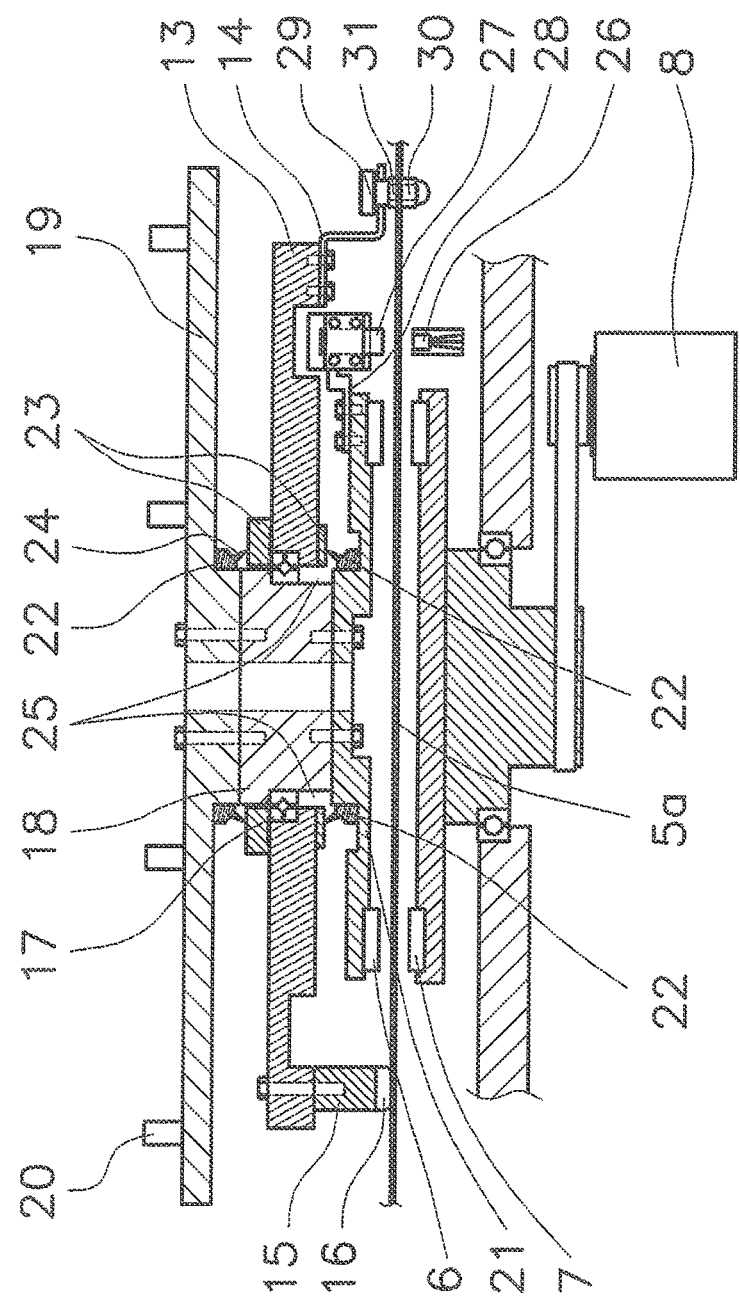
FIG. 4 is a cross-sectional view wherein the specimen table of the first example is located in a constant-temperature device.

Embodiments of the present invention will be explained particularly with reference to drawings below. FIG. 3 is an exploded view showing main members constituting a specimen table 10 of the example, and FIG. 4 is a cross-sectional view showing a situation that each member is installed in. A thermostatic chamber 5 has a closed space whose periphery is surrounded by walls, and a wall forming a bottom portion among the walls surrounding the closed space forms a floor face 5a. The specimen table 10 is so constructed that a base plate 13 of a base member is fixed on the floor face 5a of the thermostatic chamber 5 at four points with fixing brackets 14. In addition, to receive a load from upper side, the base plate 13 is supported by support blocks 15 at four points and fixed on the support blocks 15 with hexagon head bolts. A resin-made pad 16 is attached on a portion of the support block 15 where the floor face 5a comes into contact with. Besides, it is preferable to use a hexagon head bolt without a depression than a bolt having a depression at its top portion such as a bolt having a cross hole or a bolt having a hexagonal hole as a screw for fastening and fixing the members of the specimen table 10. The reasons are to spread hydrogen peroxide gas to every corner of the specimen table 10 and to facilitate wiping operation after sterilization. Further, it is preferable that the material of the pad 16 is resistant to hydrogen peroxide, and moreover, materials having a high heat resistance are more preferably used to tolerate the dry heat sterilization.

The base plate 13 has two circular holes whose diameters are different from each other at the center portion coaxially. One of the holes, which is formed to a lower side of the base plate 13, has a diameter smaller than that of an upper hole. The upper hole has a diameter such that an outer ring of the ring-shaped bearing 17 can be closely engaged, and the bearing 17 comes into contact with a bottom portion of the upper hole and is supported in a vertical direction at a position of depth of the upper hole. A columnar rotating shaft 18 is closely engaged into an inner ring of the bearing 17 from above. The rotating shaft 18 has a flange whose diameter is larger than that of the inner ring of the bearing 17 at the upper position. The flange comes into contact with an upper side of the inner ring of the bearing 17 and is supported in the vertical direction. According to this structure, the rotating shaft 18 is rotatably supported to the base plate 13 through the bearing 17.

A circular specimen plate 19 is coaxially bolted to a top face of the rotating shaft 18. Pins 20 for positioning a specimen shelf 3 are fixed on a face of the specimen plate 19 so as to correspond to the position of the bottom portion of the specimen shelf 3. In addition, a magnet plate 21 that driven magnets 6 are arranged in a circle is coaxially bolted on the bottom face of the rotating shaft 18 from below, and the specimen plate 19, the rotating shaft 18 and the magnet plate 21 are rotatably supported integrally for the base plate 13. A driving source 8 gives driving force to driving magnets 7, and rotating magnetic field penetrates the floor face 5a from lower side of the floor face 5a and is lead to the thermostatic chamber 5. A rotation center of the rotating magnetic field matches a rotation center of the rotating shaft 18. The floor face 5a is located in magnetic gap space between the driving magnets 7 and the driven magnets 6 so that the floor face 5a may not physically come into contact with both.

Accordingly, the driven magnets 6 located on the magnet plate 21 are magnetically coupled to a plurality of driving magnets 7 located at positions corresponding to the driven magnets 6 outside the thermostatic chamber 5, thereby transmitting the driving force which is given to the driving magnets 7 from the driving source 8 to the driven magnets 6, and thereby also rotating the specimen plate 19. In addition, the members exposed under the hydrogen peroxide gas atmosphere, like the base plate 13, the fixing brackets 14, the support block 15, the specimen plate 19 and the magnet plate 21, can be made of resin such as vinyl chloride and polyketone, or metal such as stainless steel or aluminum and iron subjected to an oxidation prevention treatment in order to prevent oxidation due to hydrogen peroxide. Further, a rust prevention treatment is important for each member besides the oxidation due to hydrogen peroxide because the inside of the thermostatic chamber is usually kept in a humidity equal to or more than 90% and a temperature of 37° C. while the constant-temperature device 1 is operated in culture.

The bearing 17 used in this example needs strength to support all loads of the structures such as the specimen plate 19, the rotating shaft 18 and the magnet plate 21, and the members such as the plurality of specimen shelves 3 placed on the specimen plate 19 and a plurality of containers 2 stored in the specimen shelves 3, and besides needs strength enough to rotate smoothly on supporting magnetic adsorption force due to the driving magnets 7 and the driven magnets 6 in addition to the load of the above-mentioned members.

The bearing 17 includes the outer ring, the inner ring, rolling elements arranged between the outer ring and the inner ring, and a cage for holding the rolling elements, and is widely used to rotate a shaft smoothly. Generally, a bearing made of metal such as stainless steel or iron is much used. In addition, to rotate smoothly, grease is much applied and poured around the rolling elements as a lubricant. When such a bearing is exposed to the hydrogen peroxide gas atmosphere, the metal is rusted by the oxidation due to the hydrogen peroxide gas and comes to be out of use. Further, when the grease is applied on and poured into the inside, a small amount of moisture included in the grease and moisture penetrating from the inside high humidity environment into the grease become a hotbed of bacteria. The bacteria in the moisture of the grease is not killed by the sterilization due to hydrogen peroxide gas. In addition, even if the inside of the bearing 17 is separated from the outside through a sealing member, the sealing performance is not enough. Further, rust is generated by exposing to an atmosphere of the humidity equal to or more than 90% for a long time during culture. Therefore, in the specimen table 10, is used a bearing 17 that does not need the lubricant. Specially, it is preferable to use a bearing made of resin such as PTFE (polytetrafluoroethylene), PEEK (polyetheretherketone) or PPS (polyphenylene sulfide), or a ceramic bearing made of zirconia, silicon carbide and silicon nitride considering the withstanding load and the tolerance to hydrogen peroxide.

Figure 5:
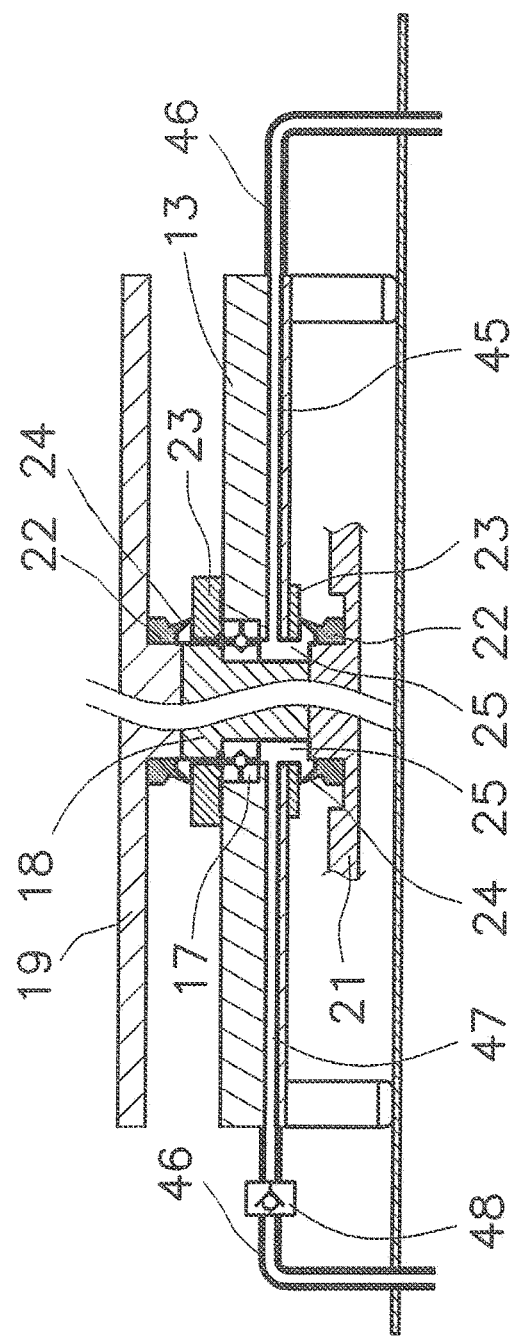
FIG. 5 is a cross-sectional view showing around a seal packing in the specimen table of a second example.

Further, in an example in which the bearing made of metal is used, the bearing 17 is protected from the hydrogen peroxide gas atmosphere or the high-humidity atmosphere by the following sealing structure. FIG. 5 shows the other example. The base plate 13 has a hole 45 opened into the space 25. The clean air is fed through a tube 46 and discharged from the thermostatic chamber through an exhaust port 47 and a check valve 48 as keeping the space 25 in positive pressure. Besides, it is preferable to use the axial loads resistance bearings such as a deep groove ball bearing, an angular ball bearing and a cross roller type bearing as for the bearing 17 because a large load is placed on the bearing 17 in its rotation center line direction. In addition, it is possible to use a thrust ball bearing or a thrust roller bearing having high strength to the load in the rotation center line direction by changing shapes of portions of the base plate 13 and the rotating shaft 18 where the bearing 17 comes into contact with.

The specimen table 10 is provided with sealing members to the bearing 17 at vertically two positions to protect the bearing 17 from the inner atmosphere. Each of the sealing members includes a ring-shaped seal packing 22 and a seal plate 23. The seal plates 23 are placed at two positions where the seal packings 22 come into contact with. The ring-shaped seal packings 22 are closely contacted and fixed to low-columnar protrusions which are respectively formed on the rotatable specimen plate 19 and the rotatable magnet plate 21, thereby being rotated integrally with the specimen plate 19 and the magnet plate 21. In addition, a seal packing 22 used in this example is a ring-shaped member having a roughly rectangular cross section, and a flange-like lip 24 is formed to an outer peripheral side of the seal packing 22 so as to extend from over the entire periphery of the ring portion. The lip 24 extends from a ring-shaped body having the roughly rectangular cross section in a height direction and in an outer peripheral direction, being formed in a taper shape in which the thickness is gradually thinned toward the tip. The space where the bearing 17 is placed is isolated from the inner atmosphere in high temperature and high humidity because the tip of the lip 24 comes into contact with the seal plate 23 over the entire periphery.

The seal packings 22 are desirably made from soft materials excellent in heat resistance and chemical resistance such as fluororubber, acrylic rubber, hydrogenated nitrile rubber, silicone resin, vinyl acetate ethylene resin, ethylene propylene rubber. In addition, it is especially desirable that the seal packings 22 are made of fluororubber with high wear resistance and little frictional resistance because the seal packings 22 come into contact with the seal plates 23 fixed to the base plate 13 over the entire periphery of the lips 24 and rotate integrally with the specimen plate 19 and the magnet plate 21.

Next, the seal plates 23 that the seal packings 22 come into contact with the lips 24 will be explained. The seal plates 23 are respectively fixed on two faces of the base plate 13 where the specimen plate 19 and the magnet plate 21 respectively face, besides being arranged coaxially with the base plate 13, each constituting a ring-shaped member. The seal plate 23 may be bolted or adhered to the specimen plate 19, however, bolting is preferable considering a replacement work of the bearing 17 because the seal plate 23 also serves to press down the outer ring of the bearing 17. In addition, the sealability is further improved by placing a packing between the seal plate 23 and the base plate 13 to closely fix the seal plate 23 and the base plate 13. Similarly, the lip 24 of the packing 22 fixed to the magnet plate 21 comes into contact with the base plate 13 or the seal plate 23. Besides, a facing direction of the lip of the ring-shaped seal packing is not limited as above, and the lip may look up and down or inward and outward. That is, the lip may come into contact with the upper protrusion of the rotating magnet plate 21 by fixing the upper packing 22 to a top face of the base plate 13, making the lip 24 contact with the lower protrusion of the rotating specimen plate 19, and fixing the lower packing 22 to an under surface of the base plate 13.

It is preferable that the seal plates 23 are made of various metals such as stainless material and aluminum material, or further fluorine resin such as polytetrafluoroethylene with a little frictional resistance or silicone resin. In case of the seal plates made of metal, it is preferable to perform surface coating treatment due to fluorine for reducing frictional resistance in addition to the surface oxidation prevention because the lips 24 of the seal packings 22 are rotated in a state of coming into contact. In addition, it is necessary for the faces of the seal plates 23 with which the lips 24 come into contact to be flat so that the lips 24 can come into contact with the seal plates 23 over the entire peripheries.

FIG. 5 is an enlarging view showing around the seal packings 22 of the specimen table 10 shown in FIG. 4. According to the above-mentioned structure, in FIG. 5, the space 25 is sealed with the members such as the base plate 13, the specimen plate 19, the magnet plate 21, the rotating shaft 18, the seal packings 22 and the seal plate 23, being isolated from the outside. Therefore, even if the thermostatic chamber 5 has the inside made in the hydrogen peroxide atmosphere, the bearing 17 is not affected by the hydrogen peroxide gas. In addition, the space 25 comes to be isolated from an atmosphere with a humidity equal to or more than 90% which is a normal culture environment. Further, to make the space 25 in a non-corrosive atmosphere, a hole 45 communicating with the space 25 is provided to the base plate 13 to introduce the gases such as clean air and dry air into the space 25.

The magnet plate 21 including the driven magnets 6 will be explained as follow. The magnet plate 21 is formed in a disk-shape, including a plurality of driven magnets 6 concentrically arranged to the side facing the floor face 5a of the thermostatic chamber. The driven magnets 6 can be fixed on the magnet plate 21 by adhesive or screws, and besides, the magnet plate 21 can be made of iron to be fixed by magnetic attraction of the driven magnets 6. In this example, as many recesses each having a size of the corresponding driven magnet 6 as the driven magnets 6 are concentrically provided to the magnet plate 21 made of iron to be engaged on the driven magnets 6 respectively, and thus constitutes fixing by the magnetic attraction. Accordingly, if the driven magnets 6 should be damaged, it is possible to easily replace with replacement parts. In addition, in case the magnet plate 21 is made of iron, there is an effect that a line of magnetic force is not be scattered. Further, it is preferable to apply nickeling resisting hydrogen peroxide on the magnet plate 21 and the driven magnets 6 as a surface treatment for preventing oxidation. Besides, it is possible to coat the driven magnets 6 with resin or paint resisting hydrogen peroxide other than nickeling, or to seal with the resin.

The magnet plate 21 is mounted to the bottom face of the rotating shaft 18 rotatably supported to the base plate 13 through the bearing 17 so that the face arranged the driven magnets 6 should face the floor face 5*a* of the thermostatic chamber 5. Here, when the drive magnets 6 are magnetically coupled with the plurality of driving magnets 7 that are placed on the positions corresponding to the driven magnets 6 outside the thermostatic chamber 5, the rotational force given from the driving source 8 to the driving magnets 7 is transmitted to the driven magnets 6 to rotate the magnet plate 21, the rotating shaft 18 and the specimen plate 19 integrally.

The specimen table 10 of this example is placed on the constant-temperature device 1 having an automatic conveyance function for automatically transporting the plurality of containers 2 stored on the plurality of specimen shelves 3 placed on the specimen plate 19 to be used. Therefore, it is necessary to accurately detect a rotating direction relative to the specimen table 10 so that a conveyor robot 12 can access the objective container 2. Then, a magnet 27 is attached to the specimen table 10 through a bracket 28. The magnet 27 is an object that a hall sensor 26 for detecting a rotational position of the constant-temperature device 1 detects a rotational position of the specimen table 10. The hall sensor 26 is a sensor using a hall effect, which converts a magnetic field generated by the magnet 27 into electrical signals and outputs the electrical signals, and besides, detects the magnetic field of the magnet 27 by penetrating a shield such as the floor face 5*a* of the thermostatic chamber 5. When memorizing the timing detected by the hall sensor 26 and the rotational position of a motor of the driving source, it is possible to move the objective specimen shelf 3 at the position accessable from the conveyer robot 12.

The specimen table 10 is installed to the thermostatic chamber 5 by making the pad 16 attached to the bottom face of the support block 15 contact with the floor face 5*a* and accurately positioned and fixed by screwing the fixing bracket 14. It is preferable to use the hexagon head bolt without a depression or a knurling screw as a screw 29 for fixing the fixing bracket 14 to control residues of bacteria as mentioned above. In addition, the atmosphere inside the thermostatic chamber 5 is prevented from leaking to the outside by welding a cup nut 30 on the floor surface 5*a* of the thermostatic chamber 5. Further, it is possible to more improve the sealability by adding a washer 31 with a seal structure to the screw 29.

Figure 6:
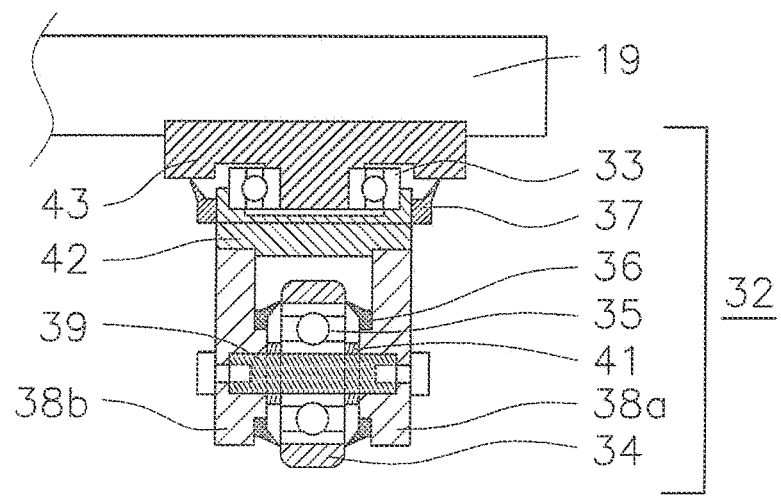
FIG. 6 is a cross-sectional view of a flexible caster of the specimen table.
Figure 6:
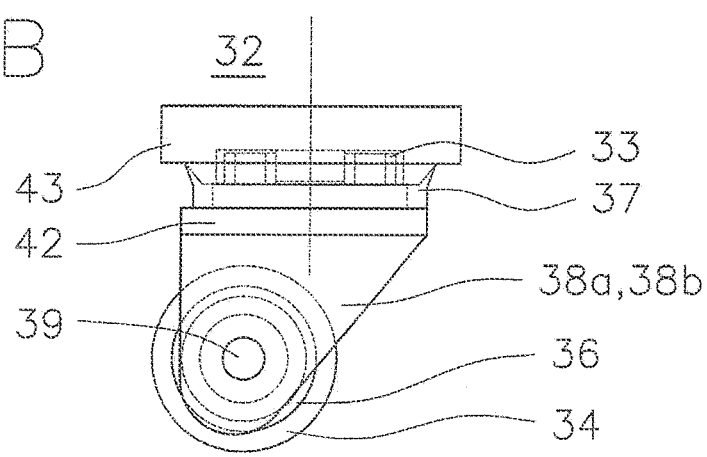
Figure 7:
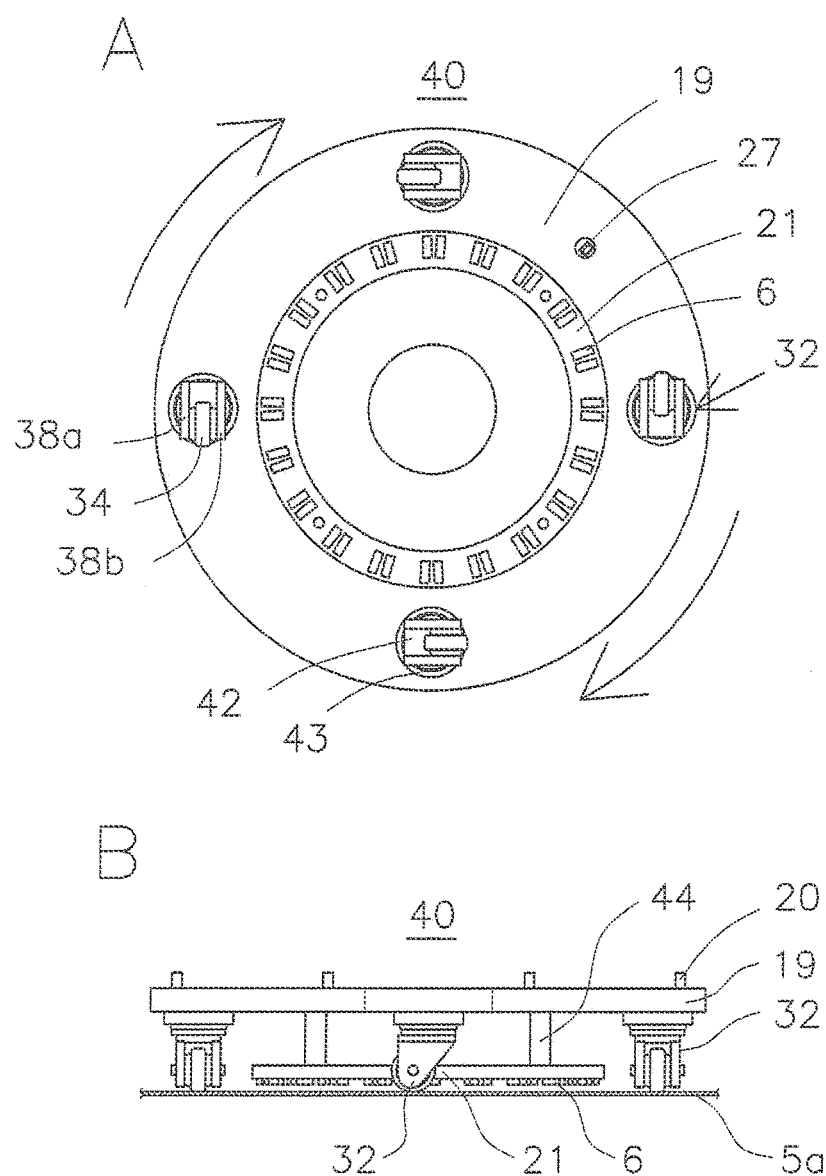
FIG. 7 is a view of the specimen table.

An example, wherein the seal packings are provided around the members made of metal such as a ball caster of the patent literature 1 or a bearing for rotatably supporting wheels made of heat resistant resin so as to prevent from being exposed to caustic agents, will be explained as a comparative example with reference to FIG. 6 and FIG. 7. A specimen table 40 in this example is provided with a plurality of universal casters 32 to the bottom face of the specimen plate 19 as a mechanism for rotating the specimen plate 19. FIG. 6A is a cross-sectional view showing a structure of a universal caster 32, and FIG. 6B is a side view. The universal caster 32 is provided with a bearing 33 for turnably holding a caster main body in a horizontal plane and a bearing 35, which is inserted into a wheel 34, for smoothly rotating the wheel 34. In addition, ring-shaped seal packings 36, 37, which have the same shape as that of the second example 2, are provided to protect each of the bearings 33, 35 from the outside atmosphere.

The bearing 35 whose outer ring is fixed on the wheel 34 has a shaft 39 whose both ends are fixed to the support blocks 38*a*, 38*b* inserted into the inner ring. In addition, at left and right of the bearing 35, a collar 41 having an external shape slightly smaller than the inner ring is inserted into the shaft 39, and contacted with and fixed on the support blocks 38*a*, 38*b*. Therefore, the wheel 34 can smoothly rotate. Low-columnar protrusions are formed to sides of the support blocks 38*a*, 38*b* where the bearing 35 faces, respectively, and the seal packing 36 is closely fixed on the low columnar protrusions. The tip of the lip part of the sealing packing 36 comes into contact with the wheel 34 over the entire periphery, thereby forming an area around the bearing 35 in a shield space, which is isolated from the outside atmosphere.

The support blocks 38*a*, 38*b* have top surfaces fixed on a caster block 42, respectively. The caster block 42 is formed into a quadrangular so that the support blocks 38*a*, 38*b* can be fixed, having a low-columnar protrusion. The sealing packing 37 is closely fixed to this low-columnar protrusion. In addition, the low-columnar protrusion has a circular cavity having almost the same diameter as the outer ring of the bearing 33. The bearing 33 is inserted into the cavity so that the half of the whole height can be filled up. The inner ring of the bearing 33 is inserted into a columnar protrusion which is formed near the center of the bottom face of a base block 43. The base block 43 has a top face fixed on the specimen plate 19 and a bottom face formed a columnar protrusion near the center. This columnar protrusion has a diameter so that the inner ring of the bearing 33 can be closely inserted and a height slightly lower than the bearing 33. Further, this columnar protrusion has a collarlike minute protrusion having a diameter slightly larger than that of the columnar protrusion formed to its root portion. When inserting the bearing 33, the inner ring comes into contact with the minute protrusion, and therefore, the outer ring can be freely rotated.

A bank is formed outside the bearing 33 of the base block 43 so as to surround the bearing 33. The lip part of the seal packing 37 comes into contact with the bank over the entire periphery, thereby forming an area around the bearing 33 in the shield space, which is isolated from the outside atmosphere. According to the above-mentioned structure, the wheel 34 is rotatably supported by the support blocks 38*a*, 38*b* through the bearing 35, and the support blocks 38*a*, 38*b* are integrally and rotatably holed to the base block 43 through the bearing 33, thereby moving the universal casters 32 and the specimen table 40 in all directions in the horizontal plane. In addition, the universal casters 32 of this example are arranged at positions where a rotation center axis of the wheel 34 and a rotation center axis of the caster block 42 are offset each other. Therefore, the wheel 34 can be constantly rotated toward the traveling direction and enables a smooth rotary motion with less frictional force. Besides, in this example, the seal packings 36, 37 are provided in order to protect the bearings 33, 35 from the outside atmosphere, however, it is also possible to provide no seal packing 36, 37 by making the bearings 33, 35 out of ceramic or resin like the former example.

The specimen plate 19 provided with the universal casters 32 will be explained in detail with reference to FIG. 7. FIG. 7A shows the specimen plate 19 of this example viewed from below, and FIG. 7B is a front view. In this example, four universal casters 32 are provided on a concentric circle whose center is positioned at the center of the circular specimen plate 19 at equal intervals, however, the number of universal casters are not restricted if it is equal to or more than three. In addition, all the universal casters 32 need not be arranged at the same distance positions from the center of the specimen plate 19. Arranging the casters 32 by being shifted in the positions does not make the trace of the wheel 34 one, thereby dispersing an influence due to the friction of the floor face 5a of the thermostatic chamber.

Inside the universal casters 32, a magnet plate 21 fixed the driven magnets 6 is mounted concentrically on the specimen plate 19 through a fixing block 44. The fixing block 44 has such a height as the driven magnets 6 should be positioned apart from the floor face 5a of the thermostatic chamber by about several millimeters, and in this example, four fixing blocks 44 are arranged. In addition, a magnet 27 is provided to the specimen plate 19 as an object of the hall sensor 26 for detecting a rotation position.

According to this structure, the driven magnets 6 are magnetically coupled with a plurality of driving magnets 7 arranged to positions corresponding to the driven magnets 6 outside the thermostatic chamber 5 by arranging the specimen table 40 of this example at a predetermined position of the floor face 5a. The rotational force given from the driving source 8 to the driving magnets 7 is transmitted to the driven magnets 6, thereby enabling to integrally rotate the magnet plate 21 and the specimen plate 19. Besides, in FIG. 7A, when an arrow direction indicates the rotational direction of the specimen plate 19, a rotation axis of the wheel 34 provided to the universal caster 32 is located back to a tuning axis of the universal caster 32 in the horizontal face. Accordingly, the specimen plate 19 can be stably rotated.

In the specimen table 40 of this example, like the first example, it is preferable to use materials which resist hydrogen peroxide atmosphere and high-humidity atmosphere for the members constituting the specimen table 40. In addition, in use of metal such aluminum or iron, it is necessary to perform surface treatment so as to resist the above-mentioned atmosphere. Further, it is preferable to perform a surface coating treatment due to a fluorine gas having small friction coefficient onto the base block 43 because the base block 43 rotates as coming into contact with the lip part of the seal packing 37. Furthermore, a face of the base block 43 where the lip portion comes into contact needs to be flat so that the lip portion can come into contact with the base block 43 over the entire periphery.

In addition, it is necessary to use materials having high strength and small friction coefficient for a wheel 35 with which the lip portion of the seal packing 36 comes into contact over the entire periphery because the wheel 35 supports the whole load of the specimen table 40 and moves on a circumferential track as coming into contact with the floor face 5a of the thermostatic chamber and rotating. Further, the wheel 35 must resist hydrogen peroxide atmosphere and high-humidity atmosphere. Therefore, it is suitable to use engineering plastics such as polyimide resin (PI), PEEK material or PPS material for the wheel 35. Furthermore, it is possible to apply the engineering plastics onto sterilization methods except for hydrogen peroxide sterilization, for example a dry-heat sterilization because many engineering plastics have heat resisting properties.

EXPLANATION OF REFERENCED NUMERALS 1 constant-temperature device
2 container
3 specimen shelf
4 specimen table (Prior Art)
5 thermostatic chamber
5a floor face
6 driven magnet
7 driving magnet
8 driving source
9 ball caster
10 specimen table (the first example)
11 lifting means
12 conveyor robot
13 base plate
14 fixing bracket
15 support block
16 pad
17 bearing
18 rotating shaft
19 specimen plate
20 pin
21 magnet plate
22 seal packing
23 seal plate
24 lip
25 space
26 hall sensor
27 magnet
28 bracket
29 screw
30 cup nut
31 washer with a seal
32 universal caster
33 bearing
34 wheel
35 bearing
36 seal packing
37 seal packing
38a support block
38b support block
39 shaft
40 specimen table (the third example)
41 collar
42 caster block
43 base block
44 fixing block
45 clean air introducing hole
46 tube
47 exhaust port
48 check valve

The invention claimed is:

1. A constant-temperature device comprises;
thermostatic chamber having a closed space and walls surrounding said closed space;
a rotating magnetic field generation means for giving a rotating field having a rotation center in a vertical axis direction from an underside of a floor face of a bottom portion of the walls to the closed space through the floor face;
a base plate detachably screwed on the floor face through brackets in the closed space of the thermostatic chamber, being supported by support blocks each having a resin-made pad at a portion where the floor face comes in contact, said pad receiving a load from upper side, wherein the base plate has a bearing having a center of a rotating shaft at a position meeting the rotation center in the vertical axis direction, a specimen plate mounted specimen shelves each saving a container storing a specimen is connected to an upper side rotating shaft over the bearing, and a magnet plate having a plurality of driven magnets is connected to the rotating shaft on a lower side of the bearing, and the driven magnets are magnetically coupled with the rotating field transmitted through the walls of the thermostatic chamber to rotate the rotating shaft in accordance with the rotating field, and;

ring-shaped seal packings each including a lip, provided to a top and a bottom of the bearing, wherein one of the seal packings is placed between the base plate and the specimen plate, and the driving magnets are placed between the magnet plate to isolate the bearing from the atmosphere of the closed space.

2. A constant-temperature device claimed in claim 1, wherein the rotating magnetic field generation means comprises a housing unit rotating at the rotation center and a plurality of driving magnets mounted on the housing unit in a state that mutual arrangement positions are regulated.

3. A constant-temperature device claimed in claim 1, wherein the ring-shaped seal packings are made of fluororubber.

4. A constant-temperature device claimed in claim 1, wherein the base plate is provided with a seal plate at a position where the lip of the ring-shaped seal packing comes into contact, said seal plate including a surface coming into contact with the lip, said surface being smoothed.

5. A constant-temperature device claimed in claim 1, wherein the base plate is provided with a pad made of heat resistant resin to a portion where the floor face of the thermostatic chamber comes into contact.

6. A constant-temperature device claimed in claim 1, wherein the base plate further comprises a flow channel for communicating an outside of the closed space to a space around a center axis, said space being isolated through the ring-shaped seal packings, and said space having a gas introduced from the outside of the closed space.

7. A constant-temperature device claimed in claim 6, wherein said gas is cleaned air.

8. A constant-temperature device claimed in claim 6, wherein said gas is nitrogen gas.

* * * * *